(12) United States Patent
Eschbach et al.

(10) Patent No.: US 12,279,915 B2
(45) Date of Patent: *Apr. 22, 2025

(54) POWERED SURGICAL INSTRUMENTS AND METHODS OF IDENTIFYING TISSUE TYPES THEREWITH

(71) Applicant: Covidien LP, Mansfield, MA (US)

(72) Inventors: Matthew Eschbach, Cheshire, CT (US); Robert H. Knapp, Middlebury, CT (US); Alexander W. Caulk, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,066

(22) Filed: Jun. 30, 2023

(65) Prior Publication Data

US 2023/0338108 A1    Oct. 26, 2023

Related U.S. Application Data

(63) Continuation of application No. 17/315,446, filed on May 10, 2021, now Pat. No. 11,690,694.

(Continued)

(51) Int. Cl.
*A61B 17/072*    (2006.01)
*A61B 17/29*    (2006.01)
(Continued)

(52) U.S. Cl.
CPC ........ *A61B 90/06* (2016.02); *A61B 17/07207* (2013.01); *A61B 17/07292* (2013.01);
(Continued)

(58) Field of Classification Search
CPC . A61B 17/068; A61B 17/0686; A61B 17/072; A61B 17/07207; A61B 17/07292;
(Continued)

(56) References Cited

U.S. PATENT DOCUMENTS 5,383,880 A    1/1995    Hooven
5,667,517 A    9/1997    Hooven
(Continued)

FOREIGN PATENT DOCUMENTS

EP    2027819 A1    2/2009
EP    2245994 A1    11/2010
(Continued)

OTHER PUBLICATIONS

European Search Report dated Oct. 19, 2021, issued in corresponding EP Appln. No. 21173738, 9 pages.
(Continued)

*Primary Examiner* — Scott A Smith

(57) ABSTRACT

A surgical instrument includes an end effector configured to clamp tissue, a motor configured to actuate the end effector, and a controller in communication with the motor and configured to determine a stress and strain of the tissue, identify a tissue type of the tissue based on the determined stress and strain of the tissue, and set an operational parameter of the surgical instrument based on the identified tissue type of the tissue.

17 Claims, 6 Drawing Sheets

Related U.S. Application Data

(60) Provisional application No. 63/027,060, filed on May 19, 2020.

(51) Int. Cl.
*A61B 90/00* (2016.01)
*G16H 20/40* (2018.01)
*G16H 40/63* (2018.01)
*A61B 17/00* (2006.01)
*A61B 17/068* (2006.01)
*A61B 34/30* (2016.01)

(52) U.S. Cl.
CPC .............. *A61B 17/29* (2013.01); *G16H 20/40* (2018.01); *G16H 40/63* (2018.01); *A61B 2017/00022* (2013.01); *A61B 2017/00398* (2013.01); *A61B 17/068* (2013.01); *A61B 17/072* (2013.01); *A61B 2017/07214* (2013.01); *A61B 34/30* (2016.02); *A61B 2090/065* (2016.02)

(58) Field of Classification Search
CPC ........ A61B 17/115; A61B 2017/00004; A61B 2017/00017; A61B 2017/00022; A61B 2017/00398; A61B 2017/00221; A61B 2017/07214; A61B 2017/2919; A61B 2017/2927; A61B 34/20; A61B 34/30
USPC .............. 227/19, 175.1, 175.2, 176.1, 180.1; 606/1, 139, 219
See application file for complete search history.

(56) References Cited

U.S. PATENT DOCUMENTS

| | | | |
|---|---|---|---|
| 5,810,811 A | 9/1998 | Yates et al. | |
| 7,032,798 B2 | 4/2006 | Whitman et al. | |
| 8,002,795 B2 | 8/2011 | Beetel | |
| 8,012,170 B2 | 9/2011 | Whitman et al. | |
| 8,808,311 B2 | 8/2014 | Heinrich et al. | |
| 8,851,354 B2* | 10/2014 | Swensgard ........... A61B 17/105 |
| | | | 227/176.1 |
| 10,052,044 B2 | 8/2018 | Shelton, IV et al. | |
| 10,251,649 B2 | 4/2019 | Schellin et al. | |
| 10,278,698 B2 | 5/2019 | Racenet | |
| 10,548,593 B2 | 2/2020 | Shelton, IV et al. | |
| 11,291,449 B2 | 4/2022 | Swensgard et al. | |
| 11,517,306 B2* | 12/2022 | Miller ................ A61B 17/0686 |
| 11,690,694 B2 | 7/2023 | Eschbach et al. | |
| 11,701,111 B2* | 7/2023 | Shelton, IV .......... A61B 17/072 |
| | | | 227/176.1 |
| 11,717,289 B2* | 8/2023 | Leimbach ........ A61B 17/07207 |
| | | | 227/175.1 |
| 11,723,657 B2* | 8/2023 | Shelton, IV ........... G16H 40/63 |
| | | | 227/176.1 |
| 11,751,869 B2* | 9/2023 | Shelton, IV ........... A61B 90/98 |
| | | | 227/180.1 |
| 11,793,514 B2* | 10/2023 | Shelton, IV .......... A61B 17/072 |
| 11,811,253 B2* | 11/2023 | Shelton ................ A61B 17/068 |
| 11,826,132 B2* | 11/2023 | Shelton, IV .......... A61B 17/295 |
| 11,849,944 B2* | 12/2023 | Shelton, IV ..... A61B 17/07207 |
| 11,850,332 B2* | 12/2023 | Shelton, IV .......... A61B 90/96 |
| 11,931,028 B2* | 3/2024 | Shelton, IV .......... A61B 17/068 |
| 11,944,338 B2* | 4/2024 | Shelton, IV .......... A61B 17/295 |
| 2004/0153124 A1 | 8/2004 | Whitman | |
| 2007/0251835 A1 | 11/2007 | Mehta et al. | |
| 2008/0251568 A1 | 10/2008 | Zemlok et al. | |
| 2008/0272172 A1 | 11/2008 | Zemlok et al. | |
| 2009/0012556 A1 | 1/2009 | Boudreaux et al. | |
| 2009/0054908 A1 | 2/2009 | Zand et al. | |
| 2009/0057369 A1 | 3/2009 | Smith et al. | |
| 2009/0076534 A1 | 3/2009 | Shelton, IV et al. | |
| 2009/0090763 A1 | 4/2009 | Zemlok et al. | |
| 2009/0108048 A1 | 4/2009 | Zemlok et al. | |
| 2009/0112271 A1 | 4/2009 | Moskowitz et al. | |
| 2010/0133318 A1 | 6/2010 | Boudreaux | |
| 2010/0270355 A1 | 10/2010 | Whitman et al. | |
| 2011/0017801 A1 | 1/2011 | Zemlok et al. | |
| 2011/0125138 A1 | 5/2011 | Malinouskas et al. | |
| 2012/0211542 A1 | 8/2012 | Racenet | |
| 2015/0134076 A1 | 5/2015 | Shelton, IV et al. | |
| 2017/0119391 A1 | 5/2017 | Schellin et al. | |
| 2018/0353659 A1 | 12/2018 | Widenhouse et al. | |
| 2019/0200981 A1 | 7/2019 | Harris et al. | |
| 2019/0201018 A1 | 7/2019 | Shelton, IV et al. | |
| 2019/0201140 A1 | 7/2019 | Yates et al. | |
| 2021/0346015 A1 | 11/2021 | Krulevitch et al. | |
| 2022/0313255 A1 | 10/2022 | Shelton, IV et al. | |

FOREIGN PATENT DOCUMENTS

| | | |
|---|---|---|
| JP | 2007-203073 A | 8/2007 |
| WO | 2019130089 A1 | 7/2019 |

OTHER PUBLICATIONS

Office Action for Japanese Patent Application No. 2021-082109 mailed Nov. 21, 2024, 4 pages.

* cited by examiner

POWERED SURGICAL INSTRUMENTS AND METHODS OF IDENTIFYING TISSUE TYPES THEREWITH

CROSS-REFERENCE TO RELATED APPLICATION

This application is a continuation of U.S. patent application Ser. No. 17/315,446 filed on May 10, 2021, now U.S. Pat. No. 11,690,694, which claims the benefit of and priority to U.S. Provisional Patent Application No. 63/027,060, filed May 19, 2020. The entire contents of the foregoing applications are incorporated by reference herein.

FIELD

The present technology relates to surgical instruments. More specifically, the present technology relates to handheld electromechanical surgical systems for performing surgical procedures having reusable components.

BACKGROUND

Linear clamping, cutting and stapling devices are used in surgical procedures to resect cancerous or anomalous tissue from a gastro-intestinal tract. Surgical staplers are used for resection and repair of abdominal and thoracic tissues. The stapler simultaneously seals and transects tissue through the use of staples and a knife. In doing so, the seal ensures that bleeding is arrested, luminal/internal content is contained, and healing is promoted.

Conventional linear clamping, cutting and stapling instruments include a pistol grip-styled structure having an elongated shaft and an end effector having a pair of gripping members disposed at a distal end of the shaft to clamp, cut, and staple tissue. Actuation of the gripping members is usually accomplished by actuating a trigger coupled to the handle, in response to which one of the two gripping members, such as the anvil portion, moves or pivots relative to the elongated shaft while the other gripping element remains fixed. The fixed gripping member includes a staple cartridge and a mechanism for ejecting the staples through the clamped tissue against the anvil portion, thereby stapling the tissue. The end effector may be integrally formed with the shaft or may be detachable allowing for interchangeability of various gripping and stapling members.

A number of surgical instrument manufacturers have also developed proprietary powered drive systems for operating and/or manipulating the end effectors. The powered drive systems may include a powered handle assembly, which may be reusable, and a disposable end effector that is removably connected to the powered handle assembly.

SUMMARY

According to one aspect of the present disclosure, a surgical instrument is provided. The surgical instrument includes an end effector having a pair of jaw members configured to clamp and staple tissue, a motor configured to actuate the end effector, and a controller in communication with the motor. The controller is configured to determine a stress and strain of the clamped tissue, identify a tissue type of the clamped tissue based on the determined stress and strain of the clamped tissue, and set an operational parameter of the surgical instrument based on the identified tissue type of the clamped tissue.

In aspects, the controller may be configured to direct the motor to move the pair of jaw members from a first state toward a second state, in which the pair of jaw members compress the tissue. The strain of the tissue may be determined as the pair of jaw members move from the first state toward the second state.

In aspects, the controller may be configured to direct the motor to maintain the pair of jaw members in the second state for a predetermined time period. The controller may be configured to monitor the stress on the tissue throughout the predetermined time period to determine a stress relaxation of the tissue.

In aspects, the controller may be configured to determine a plurality of biomechanical parameters based on the determined stress and strain of the clamped tissue and the stress relaxation of the clamped tissue. The controller may be configured to input the determined plurality of biomechanical parameters into a classification algorithm stored in a memory, whereby the controller identifies the tissue type.

In aspects, the controller may be configured to determine the stress on the tissue based on measurements of a clamping force applied to the tissue by the pair of jaw members as the pair of jaw members move from the first state toward the second state.

In aspects, the controller may be configured to determine the strain of the tissue based on measurements of a change in the thickness of the tissue as the pair of jaw members move from the first state toward the second state.

In aspects, the controller may be configured to direct the motor to maintain the pair of jaw members in the second state for a predetermined time period, monitor a stress on the tissue throughout the predetermined time period to determine a stress relaxation of the tissue, and identify the tissue type of the clamped tissue based on the determined stress relaxation of the clamped tissue and the stress and strain of the clamped tissue.

In aspects, the surgical instrument may further include a sensor associated with one or more of the pair of jaw members. The sensor may be configured to measure a physical property of the clamped tissue. The controller may be configured to determine the stress and/or strain of the clamped tissue based on the measured physical property.

In aspects, the operational parameter of the surgical instrument may include a staple size, a staple firing speed, a rate of unclamping the tissue by the pair of jaw members, a rate of clamping the tissue by the pair of jaw members, a staple firing force, and/or a clamping force of the pair of jaw members.

In accordance with another aspect, a method for operating a surgical instrument is provided. The method includes moving a pair of jaw members of an end effector from a first state to a second state, in which tissue is clamped between the pair of jaw members; determining a stress and strain of the clamped tissue as the pair of jaw members move from the first state to the second state; identifying a tissue type of the clamped tissue based on the determined stress and strain of the clamped tissue; and setting an operational parameter of the surgical instrument based on the identified tissue type of the clamped tissue.

In aspects, the method may further include maintaining the pair of jaw members in the second state for a predetermined time period; and monitoring the stress on the tissue throughout the predetermined time period to determine a stress relaxation of the tissue.

In aspects, the method may further include determining a plurality of biomechanical parameters based on the determined stress and strain of the clamped tissue and the stress relaxation of the clamped tissue; and inputting the determined plurality of biomechanical parameters into a classification algorithm stored in a memory, thereby identifying the tissue type.

In aspects, determining the stress on the tissue may include measuring a clamping force applied to the tissue by the pair of jaw members as the pair of jaw members move from the first state toward the second state.

In aspects, determining the strain of the tissue may include measuring a change in a thickness of the tissue as the pair of jaw members move from the first state toward the second state.

In accordance with yet another aspect, a surgical instrument is provided that includes an end effector having a pair of jaw members configured to clamp and staple tissue, a motor configured to actuate the end effector, and a controller in communication with the motor. The controller is configured to direct the motor to move the pair of jaw members from a first state toward a second state, in which the pair of jaw members compress the tissue; determine a stress and strain of the clamped tissue as the pair of jaw members move from the first state toward the second state; direct the motor to maintain the pair of jaw members in the second state for a predetermined time period; monitor the stress on the tissue throughout the predetermined time period to determine a stress relaxation of the tissue; and identify a tissue type of the clamped tissue based on the determined stress and strain of the clamped tissue and the determined stress relaxation of the tissue.

In aspects, the controller may be configured to set an operational parameter of the surgical instrument based on the identified tissue type of the clamped tissue. The operational parameter of the surgical instrument may include a staple size, a staple firing speed, a rate of unclamping the tissue by the pair of jaw members, a rate of clamping the tissue by the pair of jaw members, a staple firing force, and/or a clamping force of the pair of jaw members.

BRIEF DESCRIPTION OF THE DRAWINGS

Objects and features of the presently disclosed surgical system will become apparent to those of ordinary skill in the art when descriptions of various embodiments thereof are read with reference to the accompanying drawings, of which.

DETAILED DESCRIPTION

Figure 1:
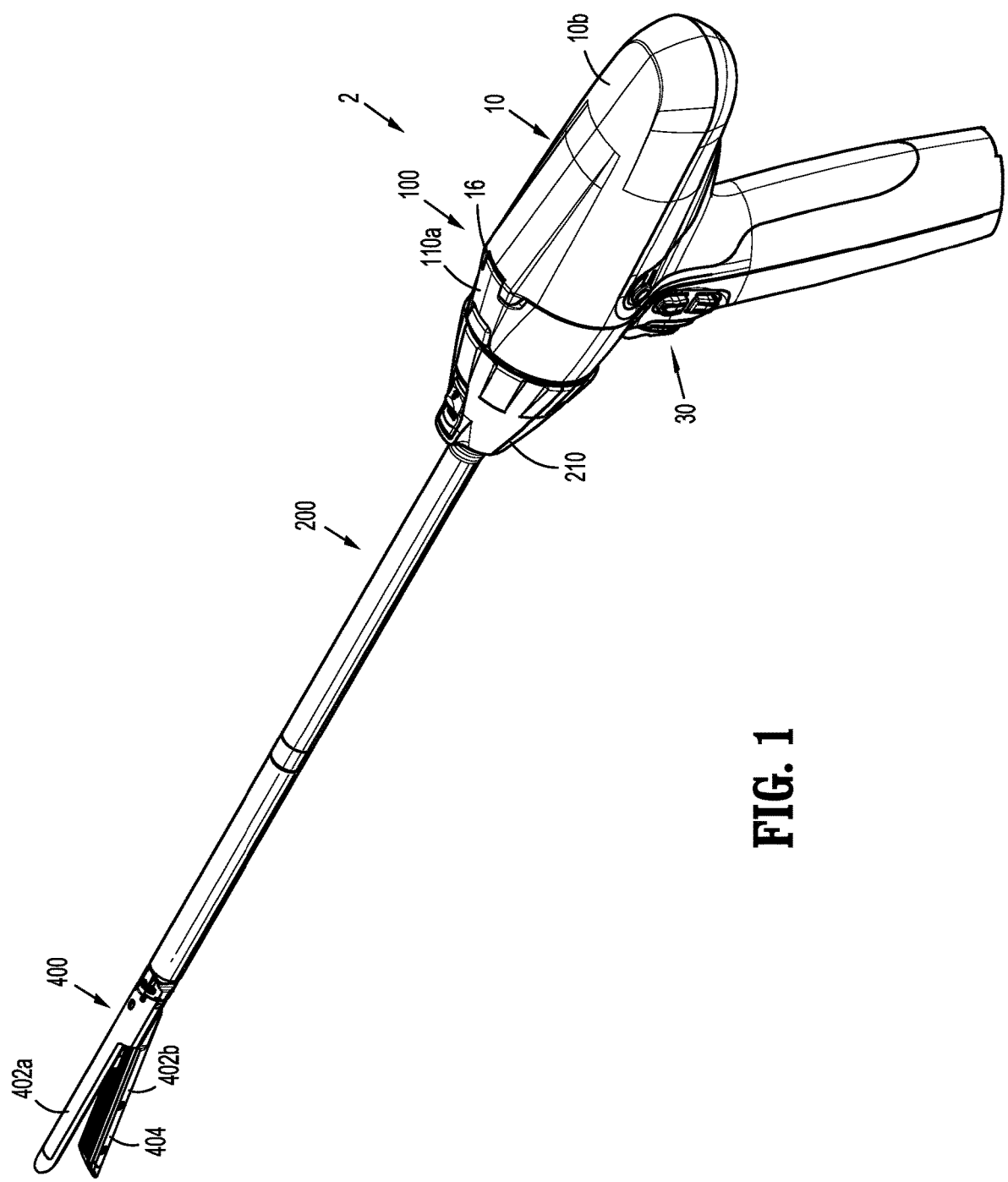
FIG. 1 is a perspective view of a surgical instrument including a powered handle assembly, an adapter assembly, and an end effector according to an aspect of the present disclosure.

Aspects of the presently disclosed surgical instruments are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

Surgical stapling is highly dependent on the biomechanics of the transected tissue. The stapler jaws seal the tissue through compression, inducing internal pressures greater than that of the blood vessels and the internal content. The compression is then held after the removal of the jaws by the formed staples. The biomechanics of the target tissue determine stapling outputs such as staple line pressure, tissue damage, hemostasis, and pneumostasis. Due to this, different organs should be stapled with specific techniques including stapler sizes, firing speeds, and clamp relaxation times. The powered staplers of the present disclosure have the ability to measure the biomechanics of tissue upon clamping of the tissue but before firing of the staples. This information can be used to classify the tissue to optimize the firing, as well as, provide information of the health of the tissue. A classification algorithm may be used to test compression and relaxation profiles of lung, stomach, colon, or other suitable types of tissue.

As illustrated in FIG. 1, a surgical instrument 2 according to the present disclosure, which is shown as a powered hand held electromechanical instrument, includes a powered handle assembly 100 configured for selective attachment to a plurality of different end effectors or single use loading units ("SULU's"), such as an end effector 400. In particular, handle assembly 100 is configured for selective connection with an adapter 200, and, in turn, adapter 200 is configured for selective connection with the end effector 400. In aspects, the end effector 400 may be operated by a robotic system rather than the powered handle assembly 100.

While a linear surgical loading unit suitable for performing endoscopic gastro-intestinal anastomosis (EGIA) procedures is shown as the end effector 400 in FIG. 1, it is contemplated that the principles of the present disclosure may be equally applicable to a surgical loading unit configured to perform end-to-end anastomosis (EEA) procedures (e.g., circular staplers), transverse stapling loading units, curved loading units, multi-use loading units ("MULU"), graspers, electrosurgical sealing forceps, rotary tissue morecellating devices, and the like.

Figure 2:
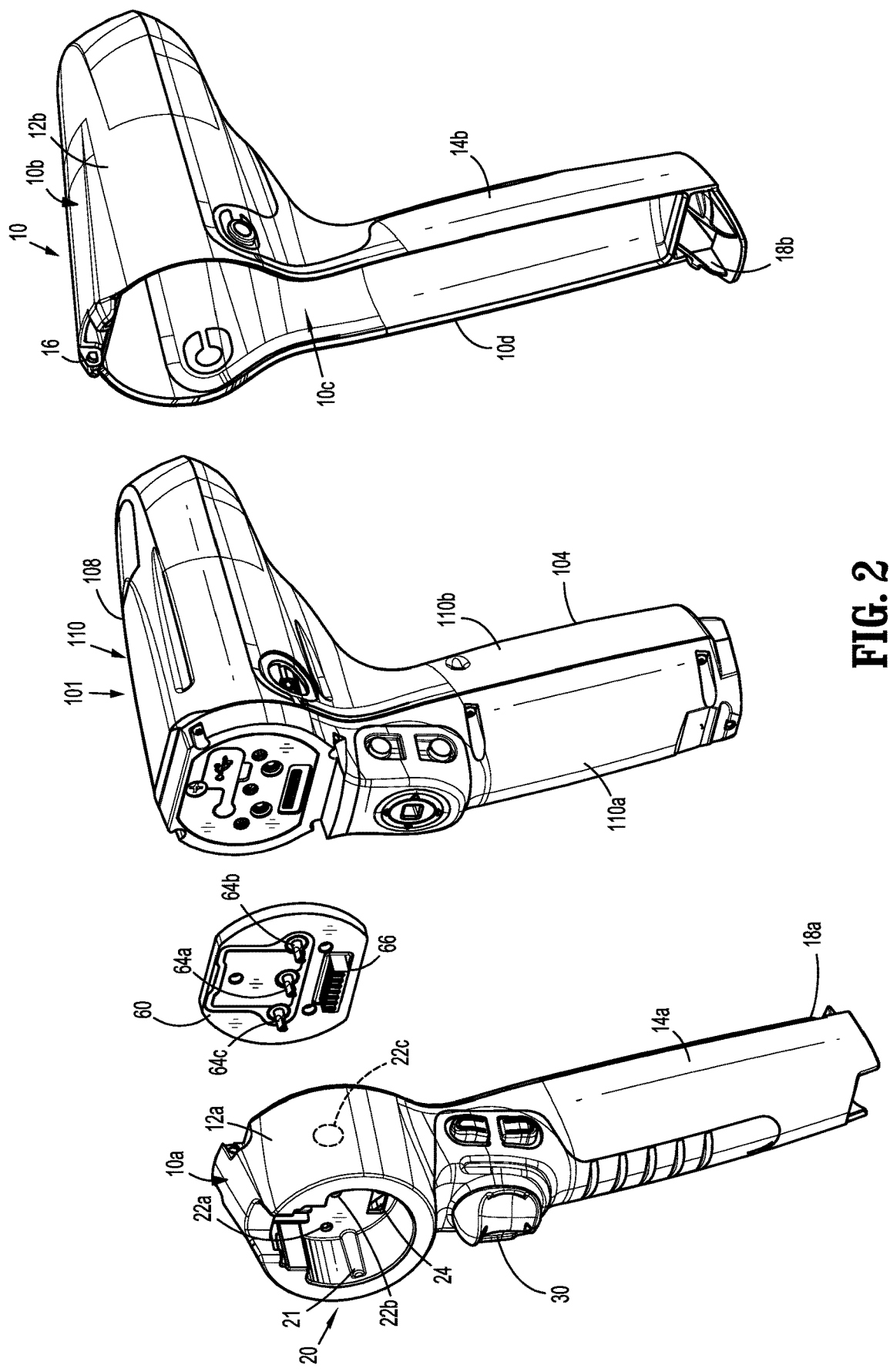
FIG. 2 is a front perspective view, with parts separated, of the handle assembly of FIG. 1.

With reference to FIGS. 1 and 2, handle assembly 100 includes a power-pack 101 (FIG. 2), and an outer shell housing 10 configured to selectively receive and enclose the power-pack 101. Outer shell housing 10 includes a distal half-section 10a and a proximal half-section 10b. The proximal half-section 10b pivotably connected to distal half-section 10a by a hinge 16 located along an upper edge of distal half-section 10a and proximal half-section 10b such that distal and proximal half-sections 10a, 10b are divided along a plane that traverses a longitudinal axis defined by adapter 200. When joined, distal and proximal half-sections 10a, 10b define a shell cavity 10c for receiving power-pack 101.

With reference to FIG. 2, each of distal and proximal half-sections 10a, 10b includes a respective upper shell portion 12a, 12b, and a respective lower shell portion 14a, 14b. Lower shell portion 14a includes a closure tab 18a configured to engage a closure tab 18b of the lower shell portion 14b to selectively secure distal and proximal half-sections 10a, 10b to one another and for maintaining shell housing 10 in a closed configuration.

Distal half-section 10a of shell housing 10 also includes a connecting portion 20 configured to couple to a corresponding drive coupling assembly 210 of adapter 200.

Specifically, the connecting portion 20 includes a recess 21 configured to receive a portion of drive coupling assembly 210 of adapter 200 when adapter 200 is mated to handle assembly 100. Connecting portion 20 of distal half-section 10a also defines three apertures 22a, 22b, 22c and an elongate slot 24 formed in a distally facing surface thereof.

Distal half-section 10a of shell housing 10 also includes a plurality of buttons such as a toggle control button 30. In aspects, toggle control button 30 may be a two-axis control stick configured to be actuated in a left, right, up and down direction. The toggle control button 30 may also be depressible. Distal half-section 10a of shell housing 10 may also support a plurality of other buttons such as a right-side pair of control buttons and a left-side pair of control button.

Shell housing 10 includes a sterile barrier plate 60 removably supported in distal half-section 10a. The sterile barrier plate 60 interconnects the power-pack 101 and the adapter 200. Specifically, sterile barrier plate 60 is disposed behind connecting portion 20 of distal half-section 10a and within shell cavity 10c of shell housing 10. Plate 60 includes three coupling shafts 64a, 64b, 64c rotatably supported therein. Each coupling shaft 64a, 64b, 64c extends through a respective aperture 22a, 22b, 22c of connecting portion 20 of distal half-section 10a of shell housing 10.

Plate 60 further includes an electrical pass-through connector 66 supported thereon. Pass-through connector 66 extends through aperture 24 of connecting portion 20 of distal half-section 10a when sterile barrier plate 60 is disposed within shell cavity 10c of shell housing 10. Coupling shafts 64a, 64b, 64c and pass-through connector 66 electrically and mechanically interconnect respective corresponding features of adapter 200 and the power-pack 101.

During use, the shell housing 10 is opened (i.e., distal half-section 10a is separated from proximal half-section 10b about hinge 16), power-pack 101 is inserted into shell cavity 10c of shell housing 10 and distal half-section 10a is pivoted about hinge 16 to a closed configuration. In the closed configuration, closure tab 18a of lower shell portion 14a of distal half-section 10a engages closure tab 18b of lower shell portion 14b of proximal half-section 10b. Following a surgical procedure, shell housing 10 is opened and the power-pack 101 is removed from shell cavity 10c of shell housing 10. The shell housing 10 may be discarded and the power-pack 101 may then be disinfected and cleaned.

Figure 3:
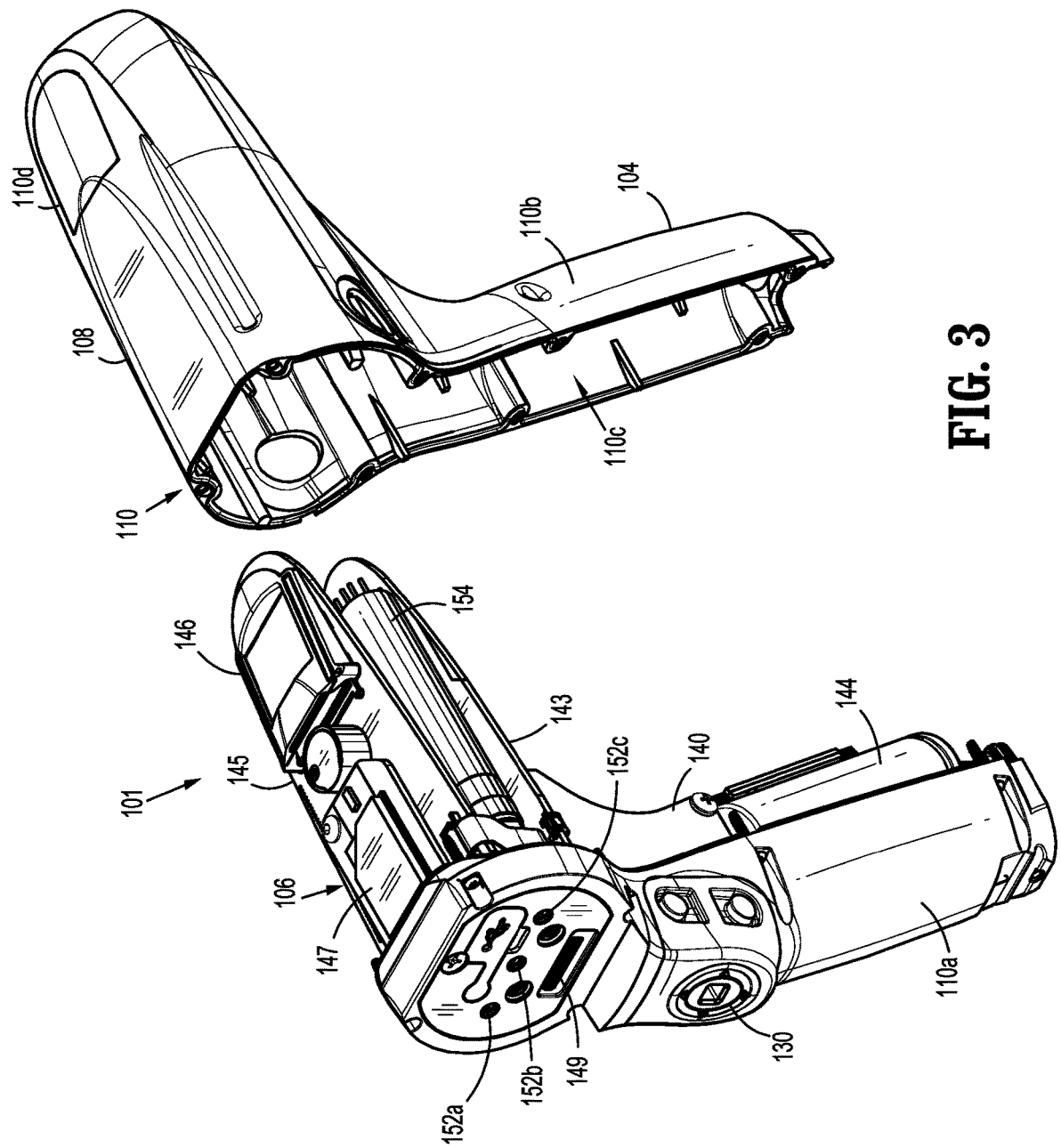
FIG. 3 is a front, perspective view of a power-pack separated from an inner rear housing of the handle assembly of FIG. 2.

With reference to FIGS. 2 and 3, power-pack 101 includes an inner handle housing 110 having a lower housing portion 104 and an upper housing portion 108 extending from and/or supported on lower housing portion 104. The inner handle housing 110 also includes a distal half-section 110a and a proximal half-section 110b, which define an inner housing cavity 110c for housing a power-pack core assembly 106. Power-pack core assembly 106 is configured to control the various operations of surgical instrument 2.

With reference to FIG. 3, distal half-section 110a of inner handle housing 110 supports a distal toggle control interface 130 that is operatively engaged with toggle control button 30 (FIG. 2) of shell housing 10, such that when power-pack 101 is disposed within shell housing 10, actuation of toggle control button 30 exerts a force on toggle control interface 130. Distal half-section 110a of inner handle housing 110 also supports various other control interfaces which operatively engage other buttons of shell housing 10.

Figure 4:
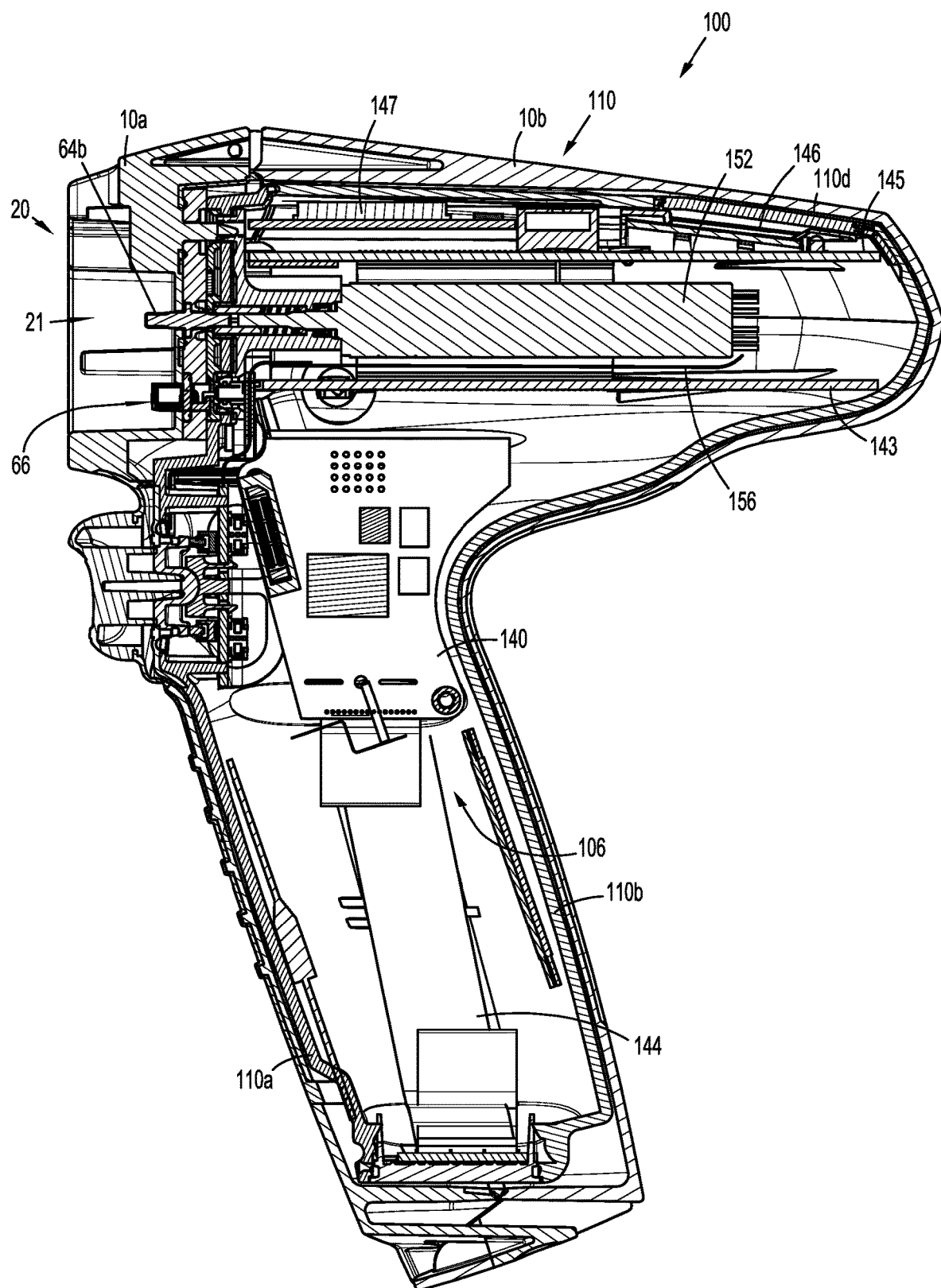
FIG. 4 is a cross-sectional view of the handle assembly of FIG. 2 taken along a section line "4-4"

With reference to FIGS. 3 and 4, power-pack core assembly 106 includes a battery circuit 140, a motor controller circuit 143, a main controller circuit 145, a main controller 147, and a rechargeable battery 144 configured to supply power to any of the electrical components of surgical instrument 2.

Power-pack core assembly 106 further includes a display screen 146 supported on main controller circuit 145. Display screen 146 is visible through a clear or transparent window 110d disposed in proximal half-section 110b of inner handle housing 110.

Power-pack core assembly 106 further includes a first motor 152 (FIG. 4), a second motor 154 (FIG. 3), and a third motor 156 (FIG. 4) each electrically connected to controller circuit 143 and battery 144. Motors 152, 154, 156 are disposed between motor controller circuit 143 and main controller circuit 145. Each motor 152, 154, 156 is controlled by a respective motor controller (not shown) that are disposed on motor controller circuit 143 and are coupled to a main controller 147. The main controller 147 is also coupled to memory 141 (FIG. 5), which is also disposed on the motor controller circuit 143. The main controller 147 communicates with the motor controllers through an FPGA, which provides control logic signals (e.g., coast, brake, etc. and any other suitable control signals). The motor controllers output corresponding energization signals to their respective motors 152, 154, 156 using fixed-frequency pulse width modulation (PWM).

Power-pack core assembly 106 also includes an electrical receptacle 149. Electrical receptacle 149 is in electrical connection with main controller board 145 via a second ribbon cable (not shown). Electrical receptacle 149 defines a plurality of electrical slots for receiving respective electrical contacts extending from pass-through connector 66 of plate 60 (FIG. 2) of shell housing 10.

Each motor 152, 154, 156 includes a respective motor shaft (not shown) extending therefrom. Each motor shaft may have a recess defined therein having a tri-lobe transverse cross-sectional profile for receiving proximal ends of respective coupling shaft 64a, 64b, 64c of plate 60 of shell housing 10.

Rotation of motor shafts by respective motors 152, 154, 156 actuates shafts and/or gear components of adapter 200 in order to perform the various operations of surgical instrument 2. In particular, motors 152, 154, 156 of power-pack core assembly 106 are configured to actuate shafts and/or gear components of adapter 200 in order to selectively actuate components of the end effector 400, to rotate end effector 400 about a longitudinal axis, to pivot the end effector 400 about a pivot axis perpendicular to the longitudinal axis defined by the adapter 200, and to close and effect a stapling function of jaw members 402a, 402b of end effector 400.

Figure 5:
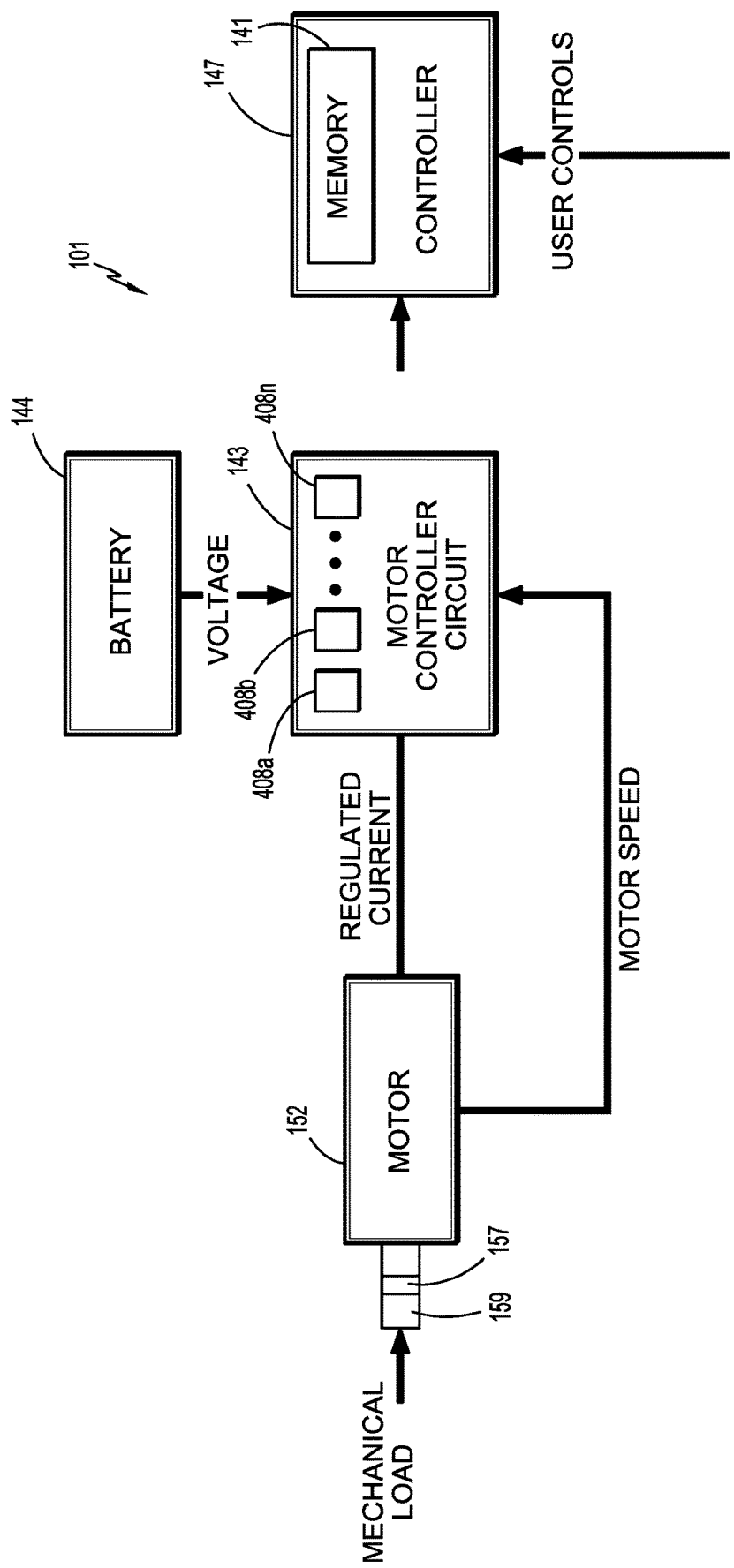
FIG. 5 is a schematic diagram of the handheld surgical instrument of FIG. 1 according to the present disclosure.

With reference to FIG. 5, a schematic diagram of the power-pack 101 is shown. For brevity, only one of the motors 152, 154, 156 is shown, namely, motor 152. The motor 152 is coupled to the battery 144. In aspects, the motor 152 may be coupled to any suitable power source configured to provide electrical energy to the motor 152, such as an AC/DC transformer.

The battery 144 and the motor 152 are coupled to the motor controller circuit 143 which controls the operation of the motor 152 including the flow of electrical energy from the battery 144 to the motor 152. The motor controller circuit 143 includes a plurality of sensors 408a, 408b, . . . 408n configured to measure operational states of the motor 152 and the battery 144. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152.

The position of various axially movable drive shafts may also be determined by using various linear sensors disposed in or in proximity to the shafts or extrapolated from the RPM measurements. It is contemplated that an optical or magnetic encoder, a linear variable differential transformer (LVDT) or other method may be used to determine the linear position of the drive shafts.

In aspects, torque may be calculated based on the regulated current draw of the motor 152 at a constant RPM. In further aspects, the motor controller circuit 143 and/or the controller 147 may measure time and process the above-described values as a function thereof, including integration and/or differentiation, e.g., to determine the rate of change in the measured values.

The motor controller circuit 143 is also coupled to the controller 147, which includes a plurality of inputs and outputs for interfacing with the motor controller circuit 143. In particular, the controller 147 receives measured sensor signals from the motor controller circuit 143 regarding operational status of the motor 152 and the battery 144 and, in turn, outputs control signals to the motor controller circuit 143 to control the operation of the motor 152 based on the sensor readings and specific algorithm instructions. The controller 147 is also configured to accept a plurality of user inputs from a user interface (e.g., switches, buttons, touch screen, etc. coupled to the controller 147).

The controller 147 is coupled to the memory 141 or any other suitable, computer-readable, non-transitory medium for storing software instructions (e.g., the algorithm) for identifying a tissue type based on biomechanical parameters of the tissue measured by the surgical instrument 2.

The present disclosure provides for an apparatus and method for assessing a stress and strain profile of tissue grasped by the end effector 400 and a stress relaxation of the grasped tissue, whereby the controller 147 of the surgical instrument 2 identifies a tissue type of the grasped tissue (e.g., lung, stomach, and colon) based on the determined stress and strain profile and stress relaxation profile. The stress measured is a compressive normal stress experienced by the tissue, and the strain measured is a compressive normal strain experienced by the tissue.

To measure the stress-strain profile and stress relaxation of tissue, the surgical instrument 2 may be equipped with a plurality of sensors. For example, jaw members 402a, 402b (FIG. 1) of the end effector 400 may include a gap measuring sensor 404 configured to determine a gap defined between the jaw members 402a, 402b, which is directly correlated with a thickness of the tissue. The gap measuring sensor 404 may be a potentiometer. In some aspects, the motor 152 may have an encoder (not explicitly shown) associated therewith configured for determining jaw angle, and therefore tissue thickness. Other methods of determining the tissue thickness (e.g., strain) of the tissue are also contemplated, such as the above-noted linear sensors disposed in or in proximity to the drive shafts of the surgical instrument 2.

To determine the stress experienced by the tissue as the jaw members 402a, 402b clamp thereabout, the surgical instrument 2 may include a strain gauge 157 (FIG. 5) associated with a main drive shaft 159. The strain gauge 157 is configured to determine the mechanical load on the drive shaft 159, which is directly correlated with the load or stress applied to the tissue. In other aspects, force measuring sensors (not explicitly shown) may be provided on tissue-contacting surfaces of the jaw members 402a, 402b. The force measured by each force measuring sensor may be converted, using known algorithms, to a value of a tension force exerted on the tissue. Other methods of determining the stress on the tissue are also contemplated. For example, the current drawn by the motor 152 may be used for detecting biomechanical properties of tissue (e.g., a stress experienced by the tissue in response to jaw clamping) since the current drawn by the motor 152 and its angular velocity change in response to the mechanical load encountered by the motor 152. Thus, analysis of the amount of change (e.g., rate of change) of current draw and angular velocity allows for determining a load or stress exerted on the tissue.

Further details about methods for measuring the stress and strain of clamped tissue may be found in U.S. Pat. No. 8,002,795, the entire contents of which are incorporated by reference herein.

By collecting stress and strain data upon clamping tissue, as well as stress relaxation data of the tissue, certain biomechanical parameters of the tissue may be determined via curve fitting the collected data using selected mathematical equations (noted below). The determined biomechanical parameters then serve as inputs to a custom classification algorithm, which identifies the type of tissue, as will be described in further detail with reference to FIG. 6.

Figure 6:
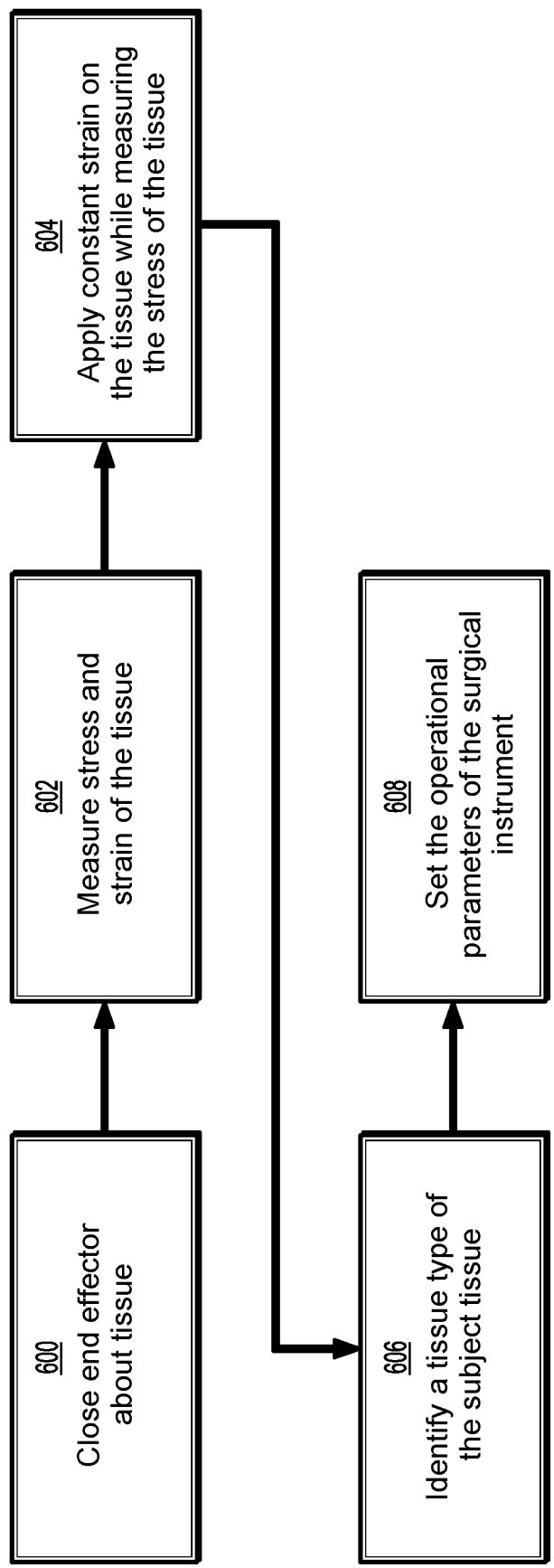
FIG. 6 is a flow chart of a method for identifying a tissue type using the surgical instrument of FIG. 1.

With reference to FIG. 6, initially, with tissue disposed between jaw members 402a, 402b, in step 600, the controller 147 signals the motor controller circuit 143 to operate the motor 152 based on desired user input, such as, for example, to control the motor 152, 154, 156 to close (without firing) the end effector 400 about tissue. The controller 147 provides the desired command to the motor controller circuit 143, which then outputs corresponding energization signals to the motor 152 to effectuate the commands received from the controller 147.

The jaw members 402a, 402b of the end effector 400 move from a first state, in which the jaw members 402a, 402b grasp (without compressing) the tissue, toward a second state, in which the jaw members 402a, 402b compress the tissue a threshold amount (e.g., to cease blood flow). The jaw members 402a, 402b may close at a constant speed of 0.31, 0.1, or 0.01 in/s. Other closing speeds are also contemplated. The jaw members 402a, 402b may be equipped with a perfusion sensor that communicates to the controller 147 when perfusion through the grasped tissue ceases to determine when to stop closing the jaw members 402a, 402b. In other aspects, the controller 147 may be configured to direct the motor 152 to close the jaw members 402a, 402b until the jaw gap is reduced by a preset percentage of the starting jaw gap (e.g., when the tissue is grasped without being compressed). For example, the controller 147 may be configured to stop the closing of the jaw members 402a, 402b upon the jaw members 402a, 402b closing to between about 10%-40% of the starting jaw gap.

As the jaw members 402a, 402b move from the first state toward the second state, in step 602, stress and strain measurements of the clamped tissue are taken at a preset time interval (e.g., at every 0.25 seconds, 0.5 seconds, or 1 second) and stored in memory 141. Determining the stress on the tissue includes measuring a clamping force (e.g., using the strain gauge 157) applied to the tissue by the pair of jaw members 402a, 402b as the pair of jaw members 402a, 402b move from the first state toward the second state and dividing the measured clamping force by a known surface area of the tissue-contacting surface of the jaw members 402a, 402b. Determining the strain of the tissue includes measuring a change in a thickness of the tissue, utilizing, for example, the gap measuring sensor 404 or the motor encoder, as the pair of jaw members 402a, 402b move from the first state toward the second state.

In step 604, the controller 147 is configured to maintain the jaw members 402a, 402b in the second state for a preset period of time to apply a constant strain on the tissue for the preset period of time. While the constant strain is applied to the tissue, measurements of the stress on the tissue are taken at a preset time interval and stored in the memory 141. The stress measurements provide a stress relaxation profile of the tissue. At this stage, the clinician may manually actuate the surgical instrument 2 to open the jaw members 402a, 402b to release the tissue. In other aspects, the controller 147 may be configured to automatically effect an opening of the jaw members 402a, 402b to release the tissue.

In aspects, the controller 147 may generate and display a stress-strain and/or a stress relaxation plot based on the received measurement data. The plots may be a collection of data points of the measurements. In further aspects, the plots may not be visualized or graphed by the controller 147 (e.g., output on a display device) and may be simply stored in the memory 141 for use by the controller 147.

In step 606, the controller 147 identifies a tissue type of the clamped tissue based on the determined stress and strain data and stress relaxation data of the clamped tissue. Identifying the tissue type includes determining a plurality of biomechanical parameters based on the determined stress and strain data and the stress relaxation data of the tissue. The biomechanical parameters are determined by curve fitting the measured stress and strain data using equations (I)-(III) below. In particular, the biomechanical parameters include Alpha and Beta from exponential equation (I), Alpha, Beta, and Gamma from exponential equation (II), and Alpha and Beta from inverse equation (III), each of which being stored in memory 141 and accessible by controller 147. In aspects, biomechanical parameters in the stress relaxation equation (IV) may also be determined by curve fitting the measured stress relaxation data to equation (IV).

$$\sigma = \beta(e^{\alpha\epsilon} - 1) \quad (I)$$

$$\sigma = \beta\left(e^{\alpha\epsilon^2} - 1\right) + \gamma\epsilon \quad (II)$$

$$\sigma = \beta\left(\frac{1}{1-\alpha\epsilon} - 1\right) \quad (III)$$

$$G(t) = c_1 e^{r_1 t} + (\sigma_0 - c_1)e^{r_2 t}, \text{ where } r_{1,2} = \frac{-A \pm \sqrt{A^2 - 4B}}{2B}. \quad (IV)$$

Upon the controller 147 determining the biomechanical parameters using equations (I)-(III) or equations (I)-(IV), the controller 147 inputs the determined biomechanical parameters into a classification algorithm stored in the memory 141, which identifies the tissue type. It is contemplated that other parameters may be used in the predictive algorithm, such as, for example, a bioimpedance of the tissue, geometric values of the tissue, and/or loading values of the tissue. The classification algorithm may be a support vector machine algorithm or an ensemble of bagged trees or any other suitable classification algorithm. It is contemplated that the memory 141 has stored therein the known biomechanical parameters of various tissue types, such as colon, lung, stomach, etc. In aspects, the controller 147 may be configured to compare the determined stress and strain data of the tissue with known stress and strain data of discrete tissue types to determine the tissue type. The controller may be further configured to compare the determined stress relaxation data of the tissue with known stress relaxation data of discrete tissue types to determine the tissue type.

In step 608, the controller 147 sets the operational parameters of the surgical instrument 2 based on the identified tissue type. The parameters set by the controller 147 may include a staple firing speed of the end effector 400, a staple firing force of the end effector 400, a clamping speed of the end effector 400, an unclamping speed of the end effector 400, a clamping force of the end effector 400, and a staple size. Other operating parameters may be stored in the memory 141 of the surgical instrument 2, such as, for example, tissue thickness indications or knife retraction speeds. The operating parameters selected by the controller 147 are those known to be best suited for the particular tissue being operated on.

The disclosure may provide a plurality of surgical loading units with each configured to be used on a specific type of tissue (e.g., liver, lung, heart, gastrointestinal, etc.) and/or during a specific type of surgical procedure (e.g., liver resection, gastro-intestinal anastomosis, lesion resection). As such, each of the loading units has a discrete set of operating parameters that are unique to the type of tissue on which the selected surgical loading unit is to be used on and/or the type of surgical procedure that the surgical loading unit is to perform. For example, if the tissue identified using the method of the present disclosure is liver tissue, the surgical loading unit having operating parameters catered to resecting liver tissue is selected. Due to liver tissue being highly vascular and thick, the surgical loading unit for liver resection may be pre-programmed with instructions, which when executed, result in a fast and constant staple firing speed regardless of a sensed tissue thickness. If another type of tissue is identified, a loading unit equipped with the appropriate operating parameters would be selected instead of the surgical loading unit used for liver resection. In aspects, the controller 147 may indicate to the clinician, either via an audio or visual cue, that the surgical loading unit may be inappropriate for the selected tissue and provide a recommendation for the appropriate surgical loading unit.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical instrument comprising:
an end effector including a pair of jaw members configured to clamp and staple tissue;
a motor configured to actuate the end effector; and
a controller in communication with the motor and configured to:
control the motor to move the pair of jaw members during a first period of time to compress the tissue until a threshold is reached;
control the motor to maintain the pair of jaw members during a second period of time, following the first period of time, to clamp the tissue under constant strain;
determine stress of the tissue while the tissue is being compressed under constant strain; and
identify a type of the tissue based on the determined stress.

2. The surgical instrument according to claim 1, further comprising:
a force sensor configured to measure clamping force as the pair of jaw members are moved.

3. The surgical instrument according to claim 2, wherein the controller is further configured to determine the stress based on the measured clamping force and a surface area of the pair of jaw members.

4. The surgical instrument according to claim 3, wherein the controller is further configured to determine the stress by dividing the measured clamping force by the surface area.

5. The surgical instrument according to claim 1, further comprising:
a thickness sensor configured to measure a change in thickness of the tissue.

6. The surgical instrument according to claim 5, wherein the thickness sensor is a gap sensor configured to measure a gap distance between the pair of jaw members.

7. The surgical instrument according to claim 1, wherein the controller is further configured to determine a stress relaxation profile of the tissue based on the stress of the tissue under constant strain.

8. The surgical instrument according to claim 7, wherein the controller is further configured to determine a plurality of biomechanical parameters of the tissue based on the stress relaxation profile.

9. The surgical instrument according to claim 8, wherein the controller is further configured to identify the type of tissue based on the plurality of biomechanical parameters of the tissue using a classification algorithm.

10. The surgical instrument according to claim 9, wherein the classification algorithm is a support vector machine learning algorithm.

11. The surgical instrument according to claim 1, wherein the controller is further configured to set an operational parameter of the surgical instrument based on the type of the tissue.

12. A surgical instrument comprising:
an end effector including a pair of jaw members configured to clamp and staple tissue;
a motor configured to actuate the end effector; and
a controller in communication with the motor and configured to:
control the motor to move the pair of jaw members to compress the tissue and maintain the pair of jaw members to clamp the tissue under constant strain;
determine stress of the tissue under constant strain; and
identify a type of the tissue based on the determined stress.

13. The surgical instrument according to claim 12, wherein the controller is further configured to determine a stress relaxation profile of the tissue based on the stress of the tissue under constant strain.

14. The surgical instrument according to claim 13, wherein the controller is further configured to determine a plurality of biomechanical parameters of the tissue based on the stress relaxation profile.

15. The surgical instrument according to claim 14, wherein the controller is further configured to identify the type of the tissue based on the plurality of biomechanical parameters of the tissue using a classification algorithm.

16. The surgical instrument according to claim 15, wherein the classification algorithm is a support vector machine learning algorithm.

17. The surgical instrument according to claim 12, wherein the controller is further configured to set an operational parameter of the surgical instrument based on the type of the tissue.

* * * * *